US00PP35566P2

(12) United States Plant Patent
Valin

(10) Patent No.: US PP35,566 P2
(45) Date of Patent: Jan. 2, 2024

(54) ***WEIGELA* PLANT NAMED 'TMWG19-28'**

(50) Latin Name: *Weigela florida*
Varietal Denomination: TMWG19-28

(71) Applicant: Branded Garden Products, Ltd., Ipswich (GB)

(72) Inventor: Charles Valin, Ipswich (GB)

(73) Assignee: Branded Garden Products, Ltd., Ipswich (GB)

( * ) Notice: Subject to any disclaimer, the term of this patent is extended or adjusted under 35 U.S.C. 154(b) by 0 days.

(21) Appl. No.: 18/185,371

(22) Filed: Mar. 17, 2023

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 5/00; A01H 6/00
See application file for complete search history.

(56) References Cited

U.S. PATENT DOCUMENTS

PP492 P * 11/1941 Cumming ..... Plt./226

* cited by examiner

*Primary Examiner* — June Hwu
(74) *Attorney, Agent, or Firm* — Weatherly IP Solutions, LLC; James M. Weatherly

(57) ABSTRACT

A new cultivar of *Weigela* plant named 'TMWG19-28' that is characterized by a compact low-growing habit, bright green foliage and white and pink flowers borne as clusters in each inflorescence, is disclosed.

2 Drawing Sheets

Figure 1:
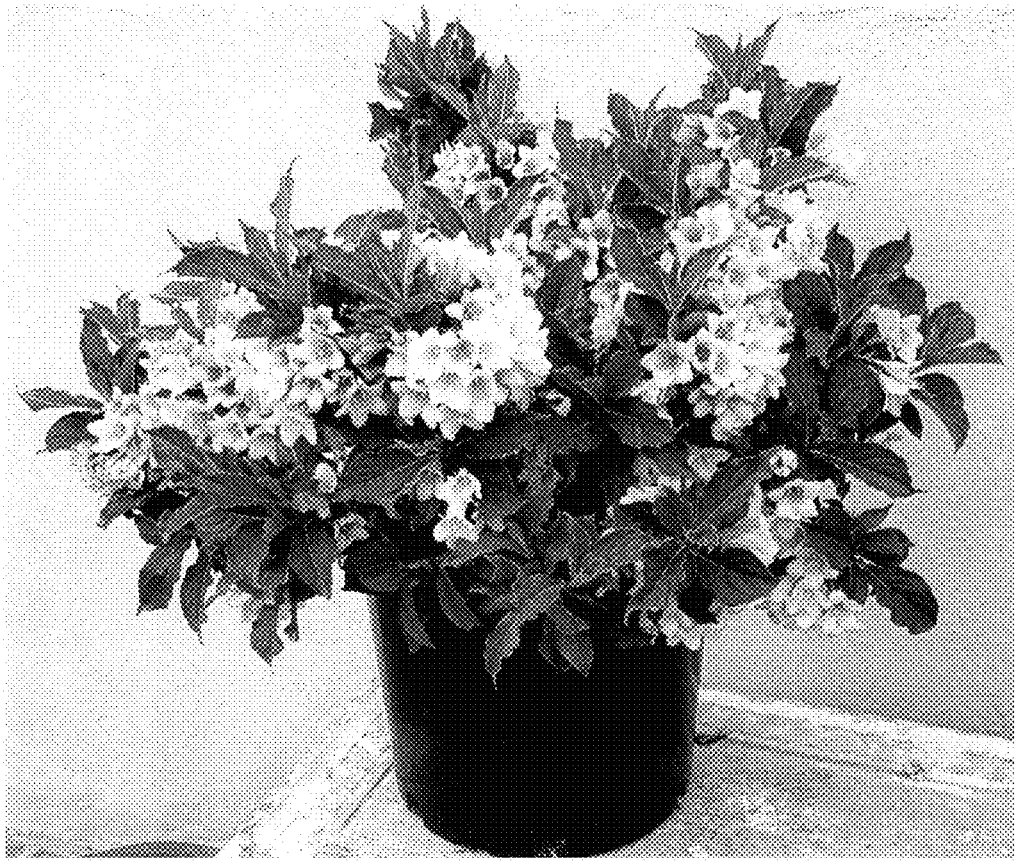

Genus and species: *Weigela florida.*
Variety denomination: 'TMWG19-28'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG19-28'.

'TMWG19-28' originated from a *Weigela* breeding program which the inventor carried out at the inventor's nursery in Ipswich, United Kingdom. The inventor had assembled a collection of *Weigela* varieties (both commercial varieties and inventor's proprietary selections). After hand pollination between many of the assembled plants, seeds were collected, sown, grown on and planted in the field for evaluation. The identities of the parents of 'TMWG19-28' are unknown.

The new cultivar 'TMWG19-28' was selected in the field in 2018 for its bright green foliage and low-growing plant habit, together with multicolored pink and white large inflorescences. 'TMWG19-28' is a colorful accent plant from spring through fall.

The inventor first asexually reproduced 'TMWG19-28' in 2018 in Ipswich, United Kingdom by the method of softwood cuttings. The inventor has determined that the unique characteristics of 'TMWG19-28' are stable and reproduce true to type in successive generations of asexual reproduction.

SUMMARY

The following traits have been repeatedly observed and represent the characteristics of the new *Weigela* cultivar 'TMWG19-28'. 'TMWG19-28' has not been tested under all possible conditions and phenotypic differences may be observed with variations in environmental, climatic and cultural conditions, however, without any variance in genotype.

1. 'TMWG19-28' exhibits a compact low-growing mounding growth habit.
2. The foliage of 'TMWG19-28' is uniformly bright green in color.
3. Mature fully flowering plants of 'TMWG19-28' achieve a height of 30 cm to 35 cm and a width of 50 cm to 55 cm.
4. Plants of 'TMWG19-28' are extremely floriferous in early to mid-spring.
5. A mature plant of 'TMWG19-28' may bear 45 flowering stems, each with a terminal cyme consisting of 7 to 14 flowers.
6. The flowers and flower buds of 'TMWG19-28' range in color and change color with age from pink to white. The entire inflorescence is multicolored.
7. Most flowers become white throughout, including their stamens and pistil. Occasional flowers and their stamens and pistil remain pink.
8. 'TMWG19-28' grows well in moist well-drained soils in full sun to partial shade.
9. 'TMWG19-28' is hardy at least to USDA Zone 5.

BRIEF DESCRIPTION OF THE PHOTOGRAPH

The accompanying color photograph illustrates the overall appearance of the new *Weigela* variety 'TMWG19-28' showing colors as true as it is reasonably possible to obtain in colored reproductions of this type. Colors in the photographs may differ from the color values cited in the detailed botanical description, which accurately describe the actual observed colors of 'TMWG19-28'.

FIG. 1 depicts a whole plant of 'TMWG19-28' in mid-April in full flower in Santa Barbara, California. The illustrated plant is three years old and is growing in a 3.7-gallon container. The illustrated plant has been grown entirely outdoors in Santa Barbara, California. No chemicals were used to treat the plant.

Figure 2:
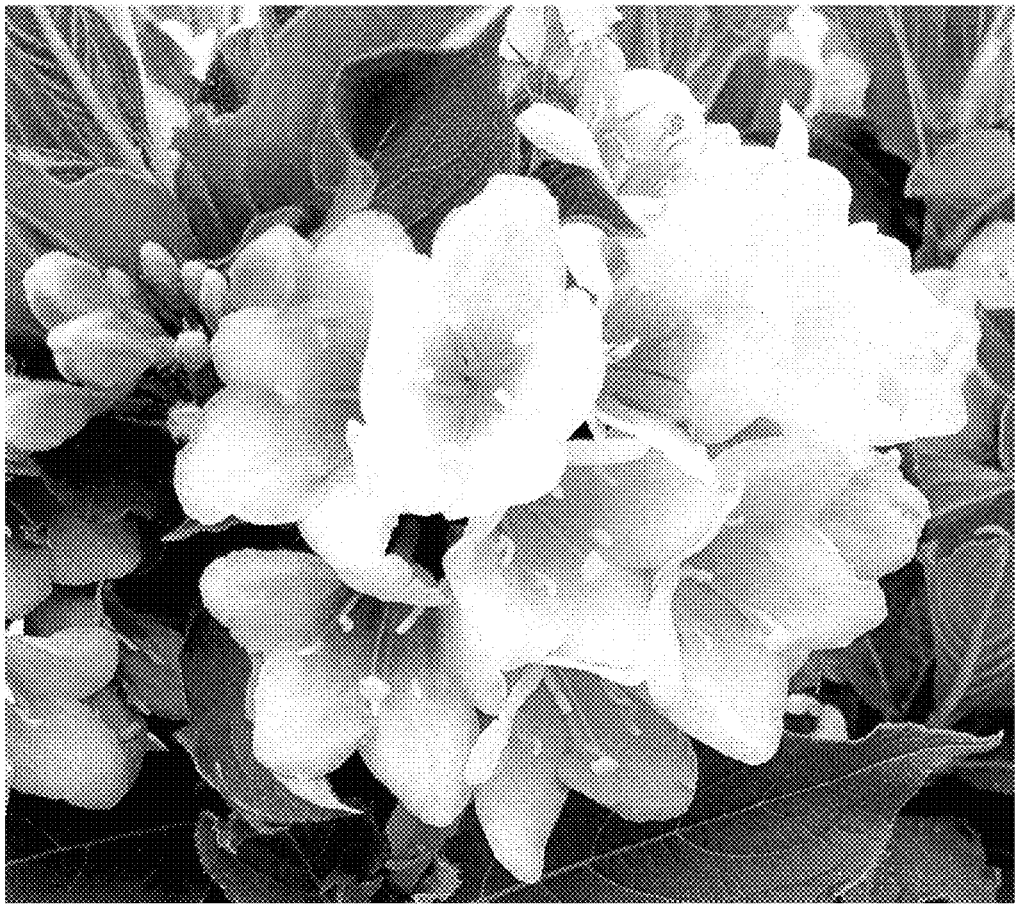

FIG. 2 depicts a close-up view of an inflorescence of 'TMWG19-28' and illustrates the varying colors of pink and white in the buds, flowers, stamens and pistil.

BOTANICAL DESCRIPTION OF THE PLANT

The following is a detailed description of the new cultivar 'TMWG19-28'. Data was collected in mid-April from fully flowering three years old plants grown in 3.7-gallon (14 liter) containers in Santa Barbara, California. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Weigela.*

Botanical classification: *Weigela.*

*Variety.*—'TMWG19-28'.

*Species.*—*florida.*

Parentage:

*Female parent.*—Unknown.

*Male parent.*—Unknown.

Plant description:

*Growth habit.*—Compact, broad mound.

*Use.*—In containers and in the landscape.

*Suitable container sizes.*—1 gallon, 3 gallon and larger.

*Dimensions.*—30 cm to 35 cm in height, and 50 cm to 55 cm in width.

*Hardiness.*—At least hardy to USDA Zone 5.

*Propagation.*—Stem cuttings.

*Time to initiate roots.*—5 to 6 weeks are required to produce roots on an initial cutting.

*Crop time.*—9-10 months to produce a first year flowering plant in a small container. Additional years to produce larger specimen plants.

*Root system.*—Fibrous.

*Light.*—Plant in full sun or partial shade.

*Soil.*—Plant in moist but well drained soil.

*Type.*—Deciduous shrub.

*Seasonal interest.*—Extremely floriferous in early-mid spring.

Stem (below first pinch or stop):

*Shape.*—Terete.

*Dimensions.*—1 cm in length, 1.0 cm in diameter.

*Color.*—197C.

*Surface.*—Lignified, rough.

Branches:

*Quantity.*—Approximately 40 primary and lateral branches.

*Branch stem dimensions.*—25 cm to 35 cm in length, 4 mm to 5 mm in diameter.

*Shape.*—Terete.

*Internode length.*—1 cm to 2.5 cm.

*Color.*—197D.

*Surface.*—Smooth, lenticels where present (lower internodes only) spaced approximately 2 mm to 6 mm apart, elliptic, length 2 mm to 6 mm, width 1.0 mm, slightly raised (less than 0.5 mm), color 197B.

Foliage:

*Leaf arrangement.*—Opposite.

*Leaf division.*—Simple.

*Leaf shape.*—Ovate, longitudinally inwardly curved.

*Leaf attachment.*—Petiolate.

*Petiole shape.*—Sulcate, adaxial surface concave.

*Petiole dimensions.*—5 mm to 6 mm in length and 3 mm in width.

*Petiole color.*—145B.

*Petiole surface.*—Pubescent, hairs fine, white NN155D, length increasing from 0.5 mm at base of leaf to 1.5 mm at stem.

*Leaf dimensions.*—72 mm in length, 36 mm in width.

*Leaf surface* (*adaxial*).—Glabrous, semi-glossy.

*Leaf surface* (*abaxial*).—Glabrous, matte.

*Leaf color* (*adaxial surface*).—137A-137B.

*Leaf color* (*abaxial surface*).—138B.

*Leaf apex.*—Narrowly acute, occasionally acuminate, tip 1.5 mm in length, recurved, color 187A.

*Leaf base.*—Cuneate.

*Leaf margin.*—Finely serrate, glabrous.

*Leaf venation pattern.*—Pinnate.

*Veins* (*adaxial surface*).—Flat, color as leaf, except midrib and lower veins 145B.

*Veins* (*abaxial surface*).—Prominent midrib and veins, increasingly raised towards base, color 145C.

Inflorescence, flowers:

*Inflorescence form.*—Terminal cyme.

*Flowers arrangement.*—From 7 to 14 flowers borne in axils of each terminal node.

*Quantity of flowers per plant.*—Approximately 300 flowers and buds at peak flowering.

*Flower aspect.*—Initially (buds and first opening) outward and upward facing, becoming horizontal and downward facing as flowers mature and age.

*Diameter of fully developed flower* (*at flower tube apex*).—34 mm as presented, 38 mm measured when flattened.

*Length of flower, including corolla tube.*—28 mm to 30 mm.

*Bud.*—Shape: Cylindrical, apex capitate. Color: 65B. Dimensions: 26 mm in length, 5 mm to 8 mm in diameter immediately prior to opening. Surface: Faintly puberulent.

*Bracteoles.*—Arrangement: Irregular, absent or borne singly or in pairs at base of peduncle. Shape: Narrowly lanceolate. Dimensions: Range from 2 mm to 13 mm in length, all are 1 mm in width at base. Color: 138B. Surface: Glabrous.

*Peduncle.*—Dimensions (buds): 5 mm to 6 mm in length and 1 mm in diameter. Dimensions (flowers): 13 mm to 15 mm in length and 1 mm in diameter. Shape: Round. Color: 145A (buds), 139C (flowers). Surface: Smooth, glossy.

*Calyx, sepals.*—Shape: Narrow funnel-shaped, clasps base of corolla tube. Calyx diameter: 4 mm measured across sepal apices. Sepals: 5 in number, free except fused at base. Sepal dimensions: 7 mm to 9 mm in length, 2 mm in width. Sepal color (adaxial surface): 144B. Sepal color (abaxial surface): 142C. Sepal surface (both surfaces): Matte, faintly puberulent.

*Flowers, general description.*—All flowers emerge from mid-pink colored buds. Most flowers open mid-pink and become pale pink and then white with age. Some flowers, approximately 2-3 out of 10, remain pink with age. The stamens and anthers of the flowers are white or pink according to the flower color itself.

*Flower* (*corolla tube, fused petals, free and flared petal lobes*.—Shape: Salverform. Dimensions: 24 mm in length, 2 mm in diameter at tube base, 12 mm in diameter at base of petal lobes, 34 mm in diameter across lobe apices. Surface: Glabrous. Color (flowers become white, both surfaces): 150D at base, becoming 65B then 65C then N155B and finally NN155D. Color (flowers remain pink, both surfaces): 150D at base, becoming 65B or 65C.

Reproductive organs:

*Number of stamens*.—5, individually fused to corolla tube at base.

*Dimensions* (*filaments*).—16 mm in length, 6 mm where fused, 10 mm free; diameter 0.75 mm to 1.0 mm in diameter.

*Filament color* (*flowers become white*).—NN155D.

*Filament color* (*flowers remain pink*).—N74B at base, becoming 65A then N155B beneath anther.

*Anther shape*.—Narrow elliptical, apex bifid.

*Anther dimensions*.—5 mm in length and 0.75 mm-1 mm in width.

*Anther color*.—161C to 161D.

*Pollen amount*.—Sparse.

*Pollen color*.—155B.

*Number of pistils*.—1.

*Style*.—Round, 35 mm in length and 0.5 mm in diameter.

*Style color* (*white flowers*).—145D at base, becoming NN155D towards stigma.

*Style color* (*pink flowers*).—N74B at base, becoming 65A then N155B beneath anther.

*Style surface*.—Glabrous.

*Stigma shape*.—Capitate.

*Stigma dimensions*.—2.5 mm in diameter and 1.5 mm in height.

*Stigma color*.—NN155A.

*Ovary*.—Not developed on any observed flowers.

Fruit: None observed.

Seed: None observed.

Susceptibility or resistance to pests and diseases: None.

COMPARISON WITH PARENT VARIETIES

The parents of 'TMWG19-28' are unknown. No comparison is available.

COMPARISON WITH KNOWN VARIETY

'TMWG19-28' may be compared with the widely grown *Weigela* variety 'Bristol Ruby' (U.S. Plant Pat. No. 492). Both 'TMWG19-28' and 'Bristol Ruby' bear bright mid-green foliage. However, whereas 'TMWG19-28' is a compact and low growing variety, 'Bristol Ruby' exhibits an erect habit and may achieve heights in excess of 2 meters in the ground. In addition, the flowers of 'TMWG19-28' are multicolored pink and white, whereas the flowers of 'Bristol Ruby' are red.

I claim:

1. A new and distinct cultivar of *Weigela* plant named 'TMWG19-28' as described and illustrated herein.

* * * * *